US009522233B2

(12) United States Patent
Bicknell et al.

(10) Patent No.: US 9,522,233 B2
(45) Date of Patent: Dec. 20, 2016

(54) INJECTION DEVICE WITH PROJECTIONS DISPOSED ON THE PASSAGE TO REDUCE THE EFFECTIVE BORE OF THE PASSAGE

(75) Inventors: Stephen Bicknell, Warwickshire (GB); Alan Peel, Lancashire (GB)

(73) Assignee: OWEN MUMFORD LIMITED, Oxford (GB)

( * ) Notice: Subject to any disclaimer, the term of this patent is extended or adjusted under 35 U.S.C. 154(b) by 384 days.

(21) Appl. No.: 13/582,749

(22) PCT Filed: Mar. 4, 2011

(86) PCT No.: PCT/GB2011/050433
§ 371 (c)(1),
(2), (4) Date: Oct. 24, 2012

(87) PCT Pub. No.: WO2011/107805
PCT Pub. Date: Sep. 9, 2011

(65) Prior Publication Data
US 2013/0035645 A1    Feb. 7, 2013

Related U.S. Application Data (60) Provisional application No. 61/312,342, filed on Mar. 10, 2010.

(30) Foreign Application Priority Data

Mar. 5, 2010   (GB) .................................. 1003667.1

(51) Int. Cl.
*A61M 5/32*    (2006.01)
*A61M 5/20*    (2006.01)

(52) U.S. Cl.
CPC ............. *A61M 5/20* (2013.01); *A61M 5/3202* (2013.01); *A61M 5/326* (2013.01); *A61M 5/3204* (2013.01);
(Continued)

(58) Field of Classification Search
CPC ................................ A61M 5/20; A61M 5/326
(Continued)

(56) References Cited

U.S. PATENT DOCUMENTS 4,976,701 A * 12/1990 Ejlersen et al. ............... 604/192
6,258,068 B1 * 7/2001 Kirchhofer ......... A61M 5/2033
128/DIG. 1
(Continued)

FOREIGN PATENT DOCUMENTS

CN    101282752 A    10/2008
CN    101420995 A    4/2009
(Continued)

OTHER PUBLICATIONS

Translation of Chinese Office Action, dated Jul. 8, 2014, from corresponding CN application.
(Continued)

*Primary Examiner* — Edelmira Bosques
(74) *Attorney, Agent, or Firm* — Young & Thompson (57) ABSTRACT

An injection device includes a cap which is withdrawn from the front of the device before use to remove a boot from the needle. The cap has fingers which grip the boot and which pass down a passage through which the needle projects to inject a dose. The passage has projections disposed to reduce the effective bore of the passage, the projections having inwardly inclined resilient portions which allow the boot to be withdrawn forwardly through the passage but prevent a finger being poked into the passage.

19 Claims, 6 Drawing Sheets

(52) U.S. Cl.
CPC  *A61M 2005/206* (2013.01); *A61M 2005/3247* (2013.01)

(58) Field of Classification Search
USPC .......................................................... 604/198
See application file for complete search history.

(56) References Cited

U.S. PATENT DOCUMENTS

| | | | |
|---|---|---|---|
| 8,647,299 | B2 | 2/2014 | Stamp |
| 2001/0049496 | A1 | 12/2001 | Kirchhofer et al. |
| 2004/0127857 | A1 | 7/2004 | Shemesh et al. |
| 2006/0036216 | A1 | 2/2006 | Rimlinger et al. |
| 2007/0265576 | A1* | 11/2007 | Pessin ........................ 604/198 |
| 2009/0326477 | A1 | 12/2009 | Liversidge |

FOREIGN PATENT DOCUMENTS

| | | |
|---|---|---|
| FR | 2 830 765 | 4/2003 |
| GB | 2434317 | 7/2007 |
| JP | 2008510547 A | 4/2008 |
| JP | 2009511177 A | 3/2009 |
| WO | 2004/043524 | 5/2004 |
| WO | 2007/047200 | 4/2007 |
| WO | 2008/093063 | 8/2008 |
| WO | 2009/081133 | 7/2009 |
| WO | 2009/114542 | 9/2009 |

OTHER PUBLICATIONS

International Search Report dated Jul. 5, 2011, corresponding to PCT/GB2011/050433.
British Search Report dated Jul. 5, 2010, corresponding to the Foreign Priority Application No. GB1003667.1.
Translation of Japanese Office Action, dated Oct. 28, 2014, from corresponding JP application.

* cited by examiner

INJECTION DEVICE WITH PROJECTIONS DISPOSED ON THE PASSAGE TO REDUCE THE EFFECTIVE BORE OF THE PASSAGE

BACKGROUND OF THE INVENTION

Field of the Invention

This invention relates to injection devices and, in particular, but not exclusively, to autoinjectors.

Description of the Related Art

In autoinjectors a syringe or cartridge (both hereinafter referred to generally as a syringe) is mounted in a body and a drive mechanism is provided so that, when the device is held against the flesh and fired, the syringe is moved forwardly to urge the needle into the injection site and thereafter the syringe plunger is advanced to expel a dose. After the dose has been expelled it is common to make the device safe, either by retracting the syringe into the autoinjector body or to extend and lock out a needle shroud from the front of the body, in each case shrouding the needle in a shrouding passage. Prior to use, the needle is usually covered by a boot to keep it sterile to prevent evaporation of the drug, and to facilitate assembly of the autoinjector, with the boot being withdrawn forwardly off the needle to prepare for an injection. In such designs it is necessary to withdraw the boot down the shrouding passage and this places conflicting demands on the designer. In order to allow the boot to be withdrawn, the shrouding passage must be wide enough to accommodate the diameter of the boot and any elements that engage a clasp the boot to remove it. Other design considerations mean that the maximum diameter of the boot is often similar to the outer diameter of the syringe barrel which may typically be 5 mm to 11 mm. Conversely, safety considerations require that the bore of the passage be sufficiently narrow to prevent a small child from pushing a finger into the open end of the shrouding passage surrounding the needle and sustaining a needle stick injury. It is therefore highly desirable to have a reduced effective aperture in the shrouding passage that still allows the boot to be withdrawn. Although particular reference is made to designs in which a boot is withdrawn axially from the needle, some similar considerations apply in general where access to the needle is to be obstructed in instances where there is no boot.

BRIEF SUMMARY OF THE INVENTION

Accordingly, in one aspect of this invention, there is provided an injection device comprising:

a body portion;

a syringe having a needle at its forward end;

one or more walls defining an elongate passage relative to which said syringe may pass between a rearward, retracted, position in which a forward tip of the needle is shrouded by said passage and a forward, extended, position in which said forward tip projects from the forward end of said passage, wherein said passage includes a plurality of transverse projections projecting inwardly from the wall of the passage to reduce the effective cross-section of the passage and at least some of the projections include resiliently deflectable portions inclined inwardly towards the forward end of the passage.

In this manner the resiliently deflectable portions reduce the effective bore of the passage and their angle of inclination means that an attempt to force access to the passage from the front end is met with resilient deflection of the projections thereby further reducing the effective diameter of the passage, whereas movement of an object in the opposite direction may deflect the projections outwardly to increase the effective bore of the passage. The term 'effective' bore is used to mean the maximum diameter of an object that may be passed down the passage in a given direction.

It is preferred for the effective bore to be slightly less than the diameter of the barrel of a syringe whereby at least some of the projections engage and exert a braking effect on the syringe, should the syringe move forwards beyond a predetermined forward position. For example, in an autoinjector, it may be required to make provision for the unlikely event that the syringe shoots forwardly beyond its intended forward position during the penetration phase, for example if the flange on the rear of the syringe barrel breaks off.

There are many various configurations for the passage; in a design where the syringe is retracted back into the autoinjector body after the injection, the passage may simply be in a forward end of the autoinjector body. In another arrangement, the walls of the passage may comprise a needle shroud element which is relatively moveable to the body portion.

Although the invention may be used where the syringe is fixed relative to a body portion, with a needle shroud movable relative to the syringe and the body portion, it is preferred for the syringe to be movable relative to the body portion from a rearward position to a forward position.

In one type of configuration, the syringe may include a boot element which covers the needle prior to use and which is withdrawable longitudinally to expose the needle. In this instance the device conveniently includes a removable cap which initially covers at least part of the front end of the device and which is removable longitudinally to withdraw the boot.

Preferably the boot has an external diameter (or maximum transverse dimension) that fits with clearance in the rearward end of said passage but which passes the forward end only on deformation of said deflectable portions.

Preferably, the cap includes a plurality of fingers which, when the cap is in its initial position, extend rearwardly down the passage to engage the boot.

Preferably, when the cap is in its initial position, the fingers on the cap alternate with the projections in the passage angularly about the longitudinal axis of the passage. Preferably they together define a rearward generally cylindrical surface that surrounds with clearance an external surface of the boot element, with the fingers extending further to provide gripping regions to engage the cap. Preferably, the passage includes support surfaces for engaging the outer surfaces of the plurality of fingers on the cap as the cap is withdrawn, thereby to prevent splaying of the fingers on the cap as the cap is withdrawn.

According to another aspect of this invention, there is provided an injection device comprising:

a body portion;

a syringe having a needle at its forward end, and a boot covering the needle;

one or more walls defining an elongate passage relative to which said syringe may pass between a rearward, retracted, position in which a forward tip of the needle is shrouded by said passage and a forward, extended, position in which said forward tip projects from the forward end of said passage, a plurality of elongate transverse projections projecting inwardly from the wall of the passage to reduce the effective cross-section of the passage, and a removable cap initially disposed at the front end of the device and having a plurality of elongate fingers which when the cap is in its initial position extend rearwardly down the passage to engage the boot, wherein said fingers are angularly interspersed with said transverse projections.

In this way the requirement for the cap fingers to extend down the shrouding passage does not require an enlarged effective bore, as the transverse projections that define the effective bore can be angularly alternated with the cap fingers.

Whilst the invention has been described above, it extends to any inventive combination of the features set out above, or in the following description or claims.

BRIEF DESCRIPTION OF THE DRAWINGS

The invention may be performed in various ways and, by way of example only, an embodiment thereof will now be described with reference to the figures, in which.

DETAILED DESCRIPTION OF THE PREFERRED EMBODIMENTS

Figure 1A:
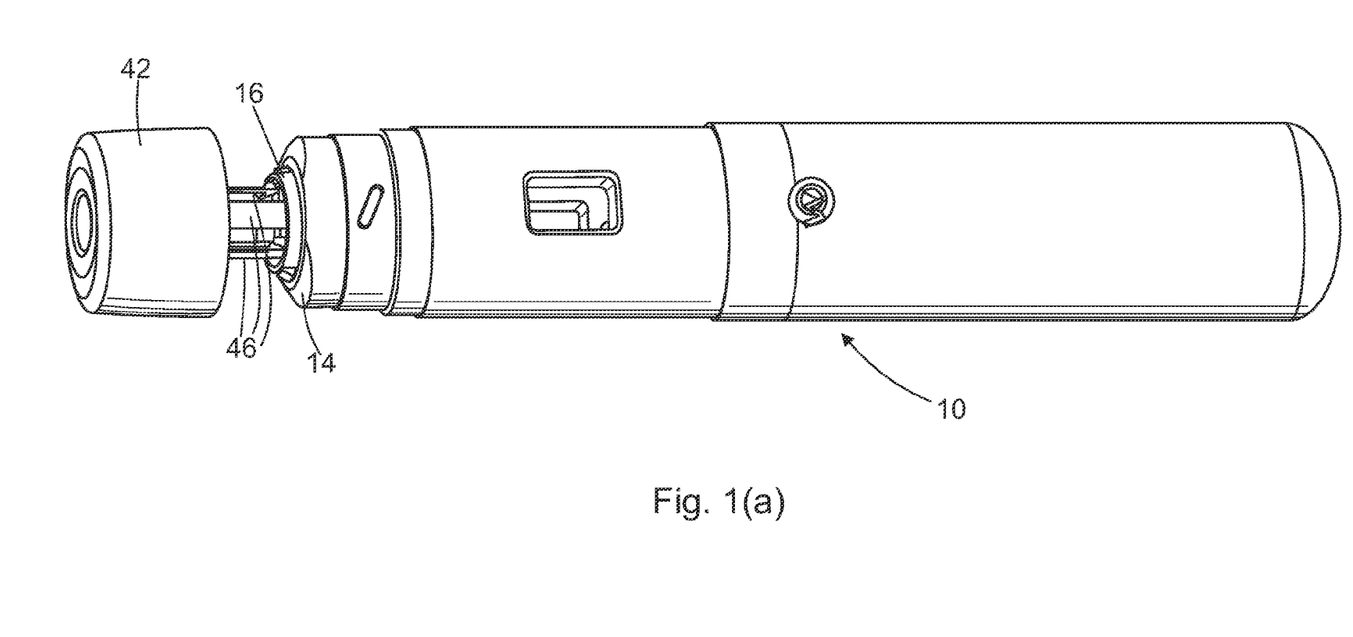
FIGS. 1(a) and (b) are a side view of an autoinjector arrangement of this invention, and a detail on the front end respectively.
Figure 1B:
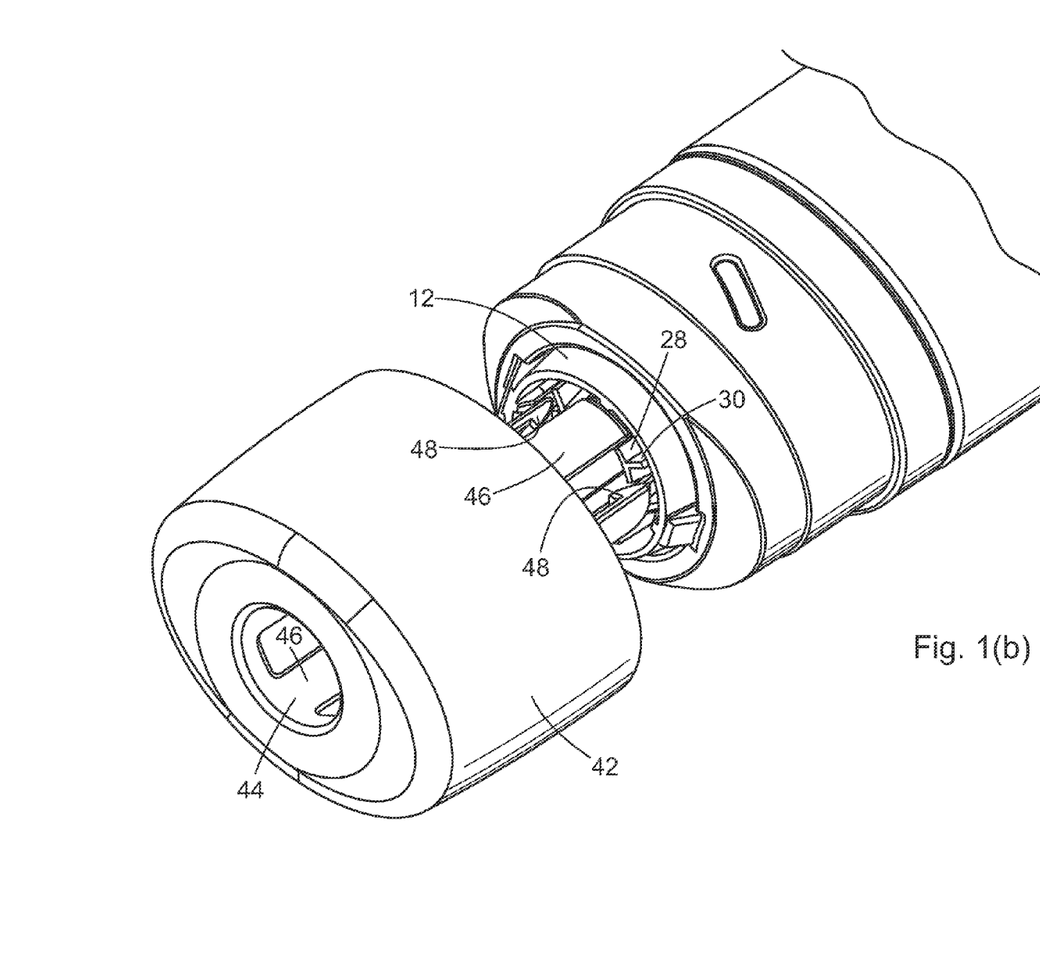

Referring initially to FIG. 1, the embodiment of autoinjector comprises a main body portion 10 containing a drive mechanism (not shown) which, when fired, urges a syringe contained within the housing forwardly so that its needle projects beyond the front end 14 of the housing to penetrate an injection site and thereafter drives a piston down the syringe to expel a dose. A needle shroud 16 is telescopically mounted on the body for movement between the extended position seen in FIG. 1 and a retracted position in which it is generally flush with the end of the housing (e.g. FIGS. 4 and 5). The needle shroud 16 is biased forwardly and, before the injection, is free to move against the spring bias but after the injection is locked out in the position shown in FIG. 1 to prevent access to the needle.

Figure 2:
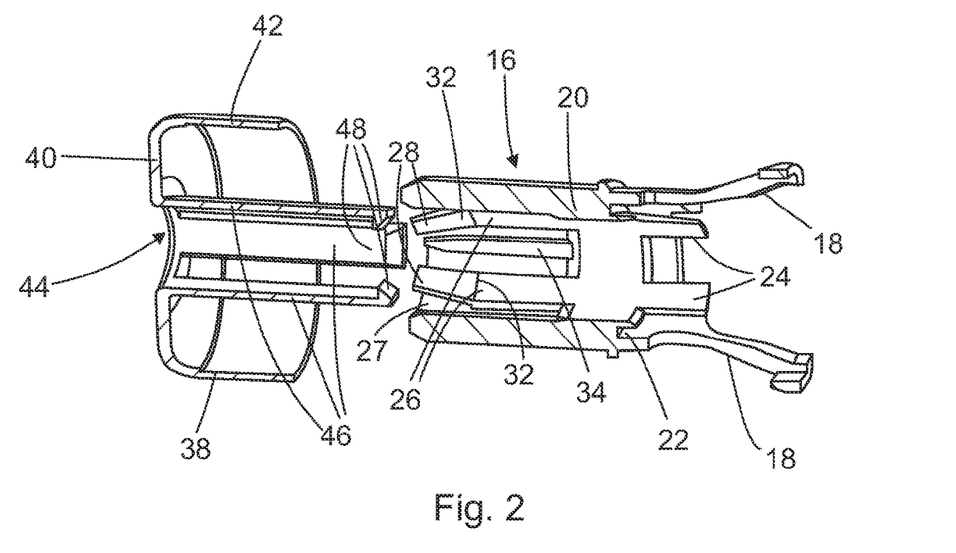
FIG. 2 is a detailed view in section showing the cap and the needle shroud when separate.

Referring now to FIG. 2, the needle shroud is of generally cylindrical form having two rearwardly divergent arms 18 which cooperate with a further mechanism (not shown) within the main body portion 10 to lock the shroud 16 in its extended position on completion of an injection. The shroud in this embodiment is formed of a one piece plastic moulding. On the inner surface of the cylindrical portion there is defined an internal collar region 20 of slightly reduced diameter. Rearwardly of the collar region is defined an annular slot 22 and four equi-spaced arcuate surfaces 24 acting as a retention and guide respectively for a compression spring (not shown) that urges the shroud forwardly. Forwardly of the collar region four transverse projections 26 extend longitudinally. For the first part of their length the projections 26 are integral with the inner surface 27 of the cylindrical portion but their forward ends 28 are free of the cylindrical surface and are therefore capable of resilient flexing movement. The forward ends 28 are inclined inwardly towards the forward end of the passage as shown. The forward ends are stiffened by a rib 30 such that they flex generally about a hinge region 32. Between each transverse projection 26 is a longitudinal guide rib 34 which cooperates with the fingers 46 on the cap as to be described below. The forward ends 28 of the transverse projections 26 are therefore designed so that an object of outer diameter less than the internal diameter of the collar region 20 but greater than the diameter defined by the forward ends of the transverse projections 26 can pass down the passage forwardly and emerge from the passage defined by the cylindrical portion on flexing of the forward ends 28. However, in the other direction, any object with a diameter greater than that defined by the forward ends 28 will contact the forward ends and tend to flex them inwards thereby further reducing the diameter of the passage.

Figure 3:
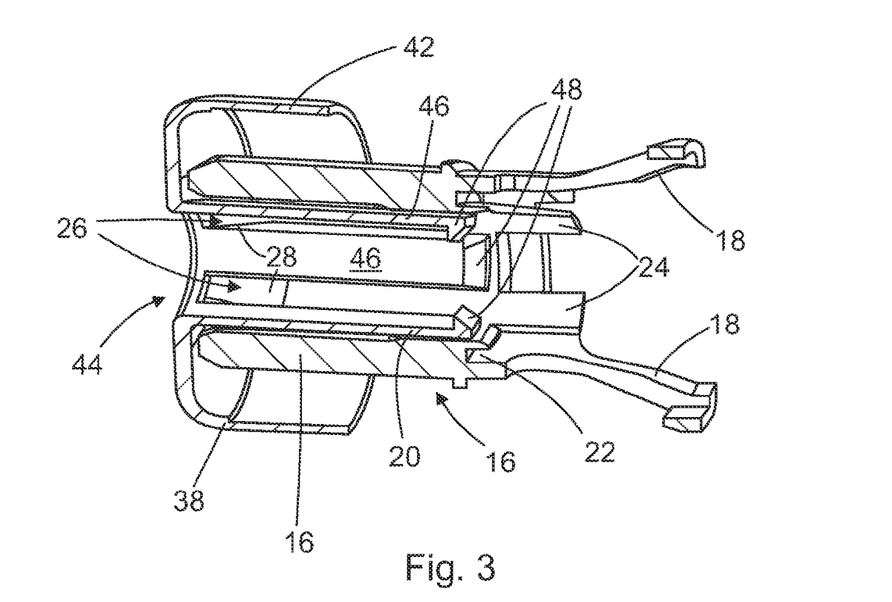
FIG. 3 is a view similar to FIG. 2 but with the cap assembled with the needle shroud.

Referring now to the cap 38, in this embodiment this is of elliptical outer cross-section to slide over a corresponding shaped forward end of the main body portion 10 of the autoinector. The cap has a flat front end 40 and a tubular elliptical skirt 42. Extending rearwardly from a circular aperture 44 in the flat front end 40 are four fingers 46 having barbs 48 at their rear ends. Each of the fingers 46 has an arcuate inner surface which, together with inner surfaces of the main parts of the transverse projections 26 defines a generally cylindrical space, when the cap is assembled in the position of FIG. 3. The outer surfaces of the fingers 46 slide over respective guide ribs 34 on the inner surface of the shroud to constrain the fingers 46 against splaying. Furthermore, the inner surface of the collar 20, being of slightly reduced diameter, further constricts the fingers 46 to urge them more tightly against the boot during the initial phases of boot removal.

Figure 4A:
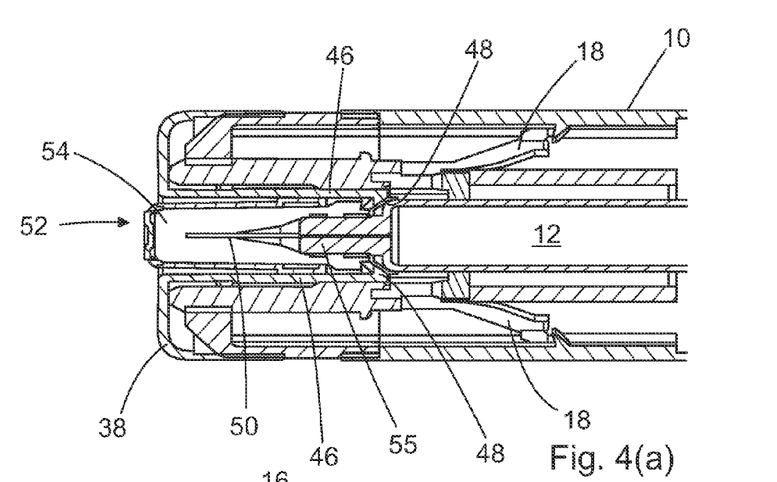
FIG. 4(a) is a section view through the front end of the device as supplied with the cap and boot in their initial positions.
Figure 4B:
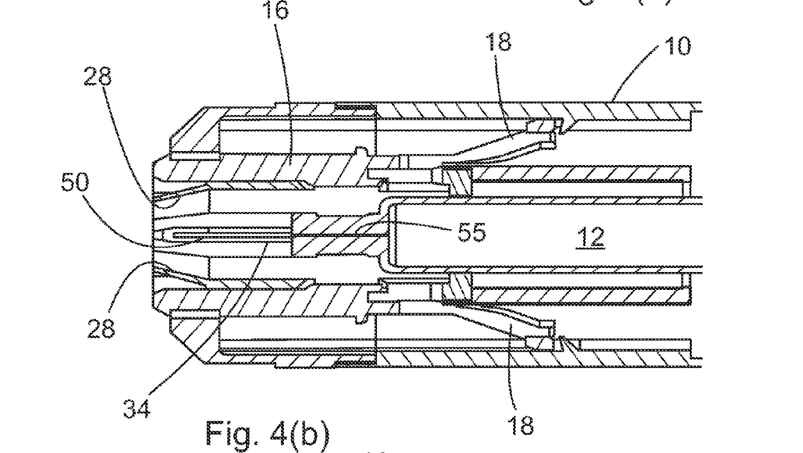
FIG. 4(b) is a view similar to FIG. 4(a) but with the cap and boot removed, and the shroud in a retracted position.
Figure 4C:
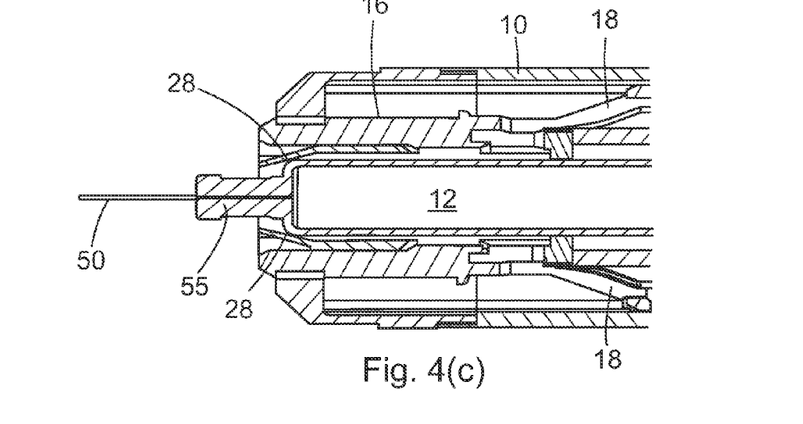
FIG. 4(c) is a view similar to FIG. 4(b) but showing the syringe in an overshoot position.
Figure 5A:
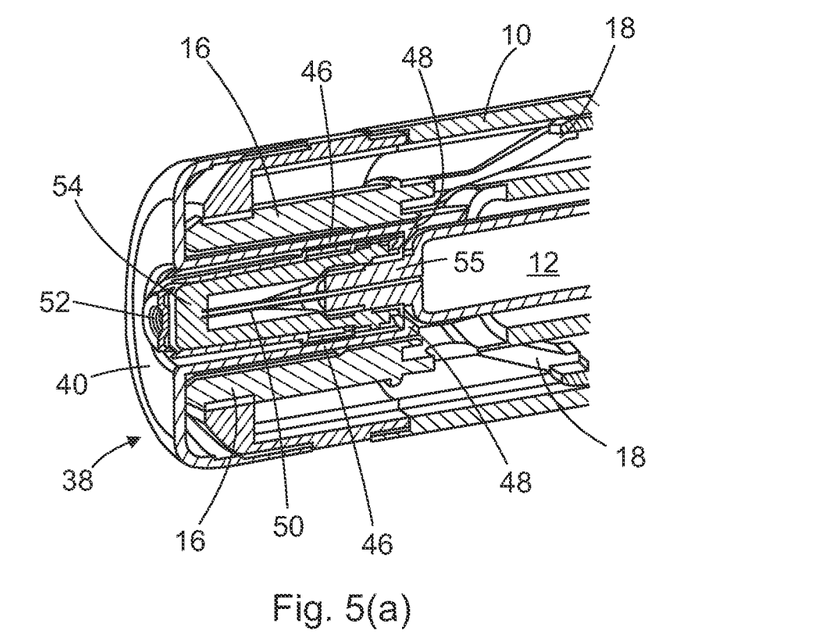
FIG. 5(a) is an isometric section view through the front end of the device showing the cap and boot in the condition as supplied.
Figure 5B:
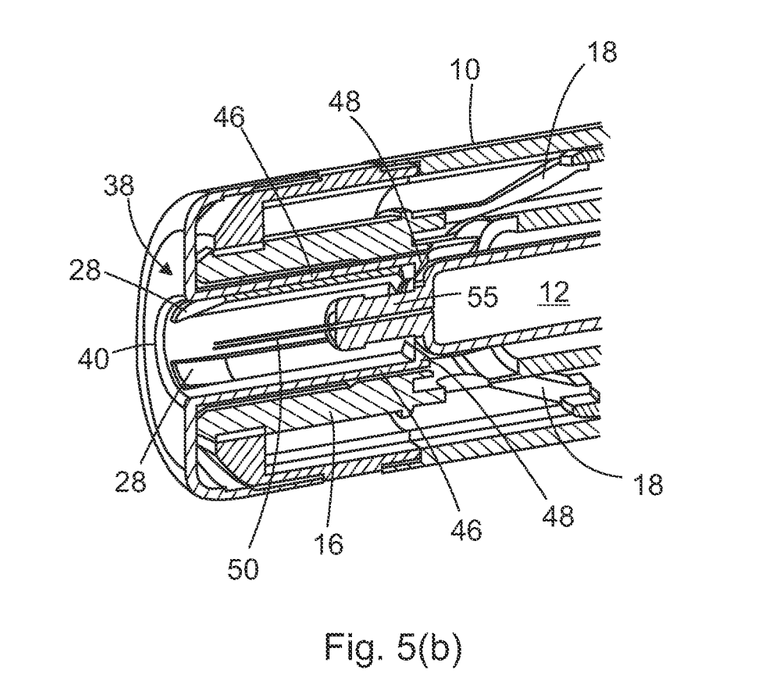
FIG. 5(b) is a view similar to FIG. 5(a) except with the boot removed for clarity.

Referring now to FIGS. 4(a) to (c) and 5(a) to (d), in FIGS. 4(a) and 5(a) the front end of the autoinjector is shown in the condition as supplied. Thus the needle 50 of the syringe is covered by a boot 52 including an insert 54 of soft rubber material which seals around the spigot 55 at the front end of the barrel of the syringe to keep the needle sterile. In this condition the barbs 48 on the fingers 46 of the cap 38 engage behind a rearwardly facing shoulder on the rear end of the boot 52 and are constrained against radially outward movement by the constriction provided by the collar region 20 as aforesaid.

In order to prepare for an injection, the cap 38 is slid forwardly off the front end of the housing 10 and in doing so the boot 52 is pulled off the syringe needle 50.

Figure 5C:
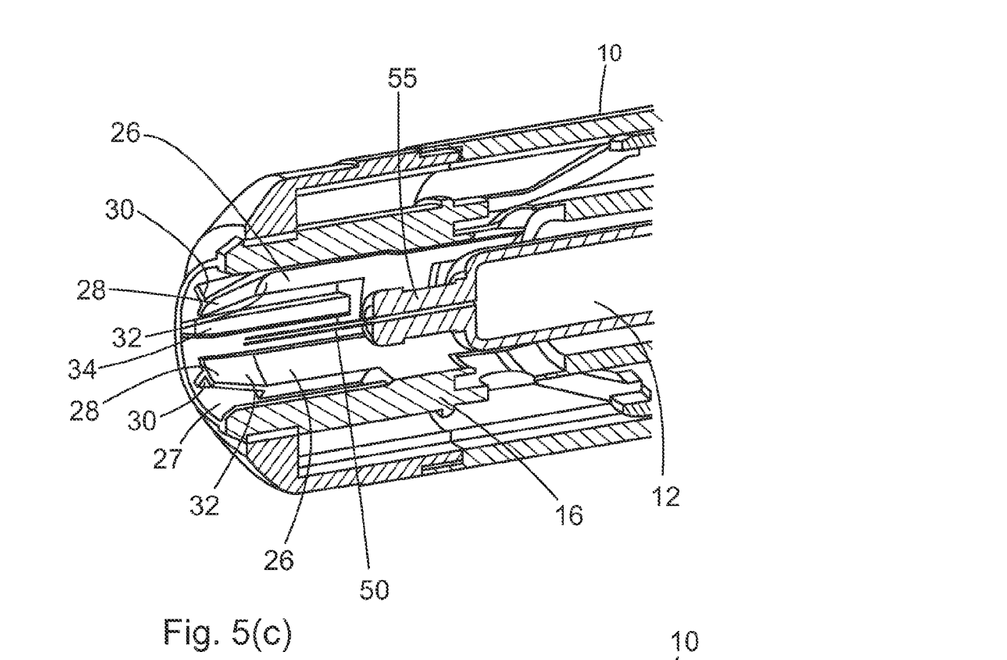
FIG. 5(c) is a view showing the cap and boot removed.

Removing the cap also allows the needle shroud 16 to move forwardly under the influence of the compression spring. However the shroud can retract into the housing against the spring when the device is pressed against an injection site, as shown in FIG. 4(b) and FIG. 5(c) ready for injection. However it is important also to ensure, for safety, that it is not possible for a child to push their finger into the needle shroud and contact the needle. The front ends 28 of the transverse projections 26 are therefore designed so that they can expand a little to allow the boot 52 to be passed forwardly down the passage and removed but then return to a smaller diameter in which they define a smaller bore and which tends to further close if an attempt to made to pass a fingertip into the bore.

Figure 5D:
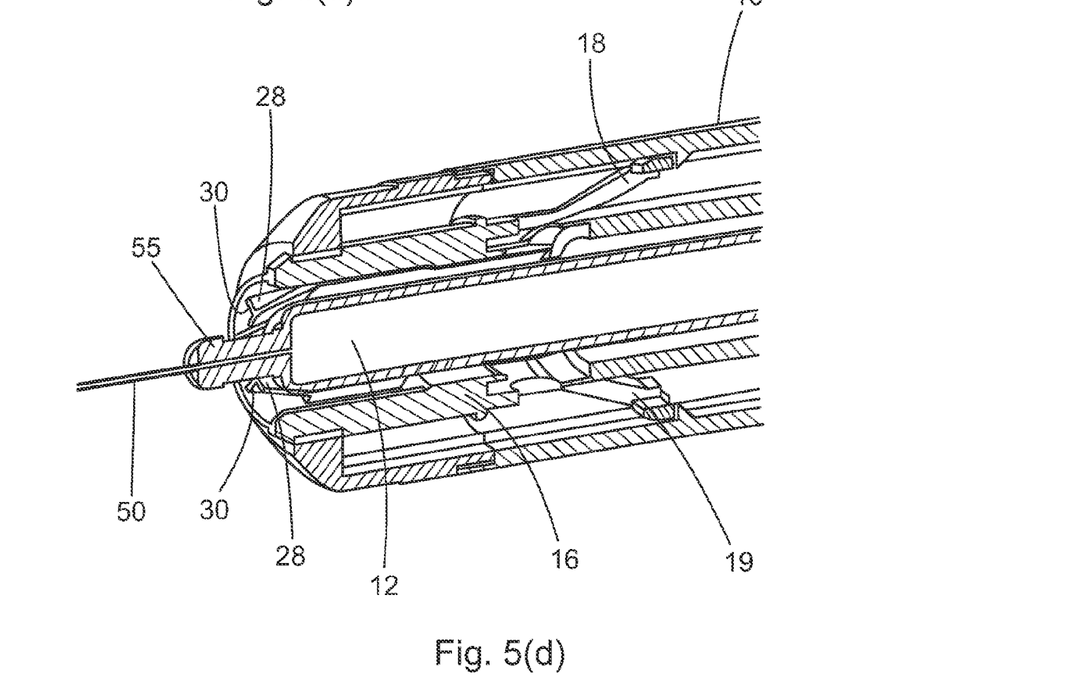
FIG. 5(d) is a view with the syringe in an overshoot position.

In addition, as shown in FIG. 4(c) and FIG. 5(d) the forward ends 28 also perform an important safety function in the unlikely event that the syringe over-extends during the penetration phase. This may for example occur if the flanges on the rear end of the syringe barrel break off. Should this happen, the syringe movement will be slowed and arrested by the inwardly directed forward ends 28 of the transverse projections thus retaining the syringe 12 in the device.

If required, the resilient flexing movement of the free ends 28 may be reinforced by means of a circlip or the like of e.g. metal spring material to mitigate again possible plastic creep if the device is to be stored for long periods.

The invention claimed is:

1. An injection device comprising:
   a body portion;
   a syringe having a forward end and a needle at the forward end; and
   one or more walls defining a passage extending from a rearward end to a forward end and relative to which said syringe may pass between a rearward, retracted position in which a forward tip of the needle is located within an interior of the passage rearward of said forward end so as to be shrouded by said passage and a forward, extended position in which said forward tip projects from the forward end of said passage,
   wherein said passage includes a plurality of transverse projections within the interior of said passage and projecting inwardly from an inner surface of the wall of the passage at an intermediate position between said forward end and rearward end of the passage to reduce an effective cross-section of the passage, the projections including resiliently deflectable portions inclined inwardly towards the forward end of the passage, and
   wherein at least forward ends of all of the resiliently deflectable portions are forward of the forward tip of the needle when the syringe is in the rearward, retracted, position, and
   wherein the walls of the passage are defined by a needle shroud element which is movable relative to the body portion and forwardly biased, such that when the syringe is in the forward extended position, the needle shroud element may move to an extended position in which the forward tip of the needle is located within the interior of the passage rearward of said forward end so as to be shrouded by said passage.

2. The injection device according to claim 1, wherein a transverse dimension of a cross-section of the forward end of the passage is less than the diameter of a barrel of said syringe whereby the projections engage and exert a braking effect on the syringe should the syringe move forwards beyond a predetermined forward position.

3. The injection device according to claim 2, wherein said syringe is movable relative to the body portion from a rearward position to a forward position.

4. The injection device according to claim 2, wherein the syringe includes a boot element which covers the syringe needle and which is withdrawable longitudinally to expose the needle, the injection device further including a removable cap which initially covers at least part of the front end of the device and which is removable longitudinally to withdraw the boot.

5. The injection device according to claim 1, wherein said syringe is movable relative to the body portion from a rearward position to a forward position.

6. The injection device according claim 1, wherein the syringe includes a boot element which covers the syringe needle and which is withdrawable longitudinally to expose the needle, the injection device further including a removable cap which initially covers at least part of the front end of the device and which is removable longitudinally to withdraw the boot.

7. The injection device according to claim 6, wherein said boot element has an outer maximum transverse dimension receivable within a rearward end of said passage with a clearance being present between the boot element and the rearward end of said passage, the maximum transverse dimension being greater than a cross-section of the forward end of said passage, said boot element being passable through the forward end of said passage on deflection of said deflectable portions.

8. The injection device according to claim 7, wherein said cap includes a plurality of fingers which, when the cap is in its initial position, extend rearwardly down the passage to engage the boot.

9. The injection device according to claim 6, wherein said cap includes a plurality of fingers which, when the cap is in its initial position, extend rearwardly down the passage to engage the boot.

10. The injection device according to claim 9, wherein the fingers on the cap alternate with the projections in the angular direction about the longitudinal axis of the passage.

11. The injection device according to claim 10 wherein the transverse projections and the fingers each have inner arcuate surfaces that together define a rearward generally cylindrical surface that surrounds an external surface of said boot element with a clearance being present between the external surface of said boot element and the rearward generally cylindrical surface.

12. The injection device according to claim 9, wherein said passage includes support surfaces for engaging outer surfaces of the plurality of fingers on the cap as the cap is withdrawn.

13. The injection device according to claim 1, wherein an attempt to force access to the passage from the front end causes resilient deflection of the resiliently deflectable portions to further reduce the effective bore of the passage.

14. The injection device according to claim 1, wherein the needle shroud element is telescopically mounted on the body.

15. The injection device according to claim 1, wherein the needle shroud element is initially held against the forward bias in the rearward retracted position whereby the forward end of the needle shroud element is proximal to a forward end of the housing.

16. An injection device comprising:
   a body portion; a syringe having a forward end, a needle at the forward end, and a boot covering the needle; one or more walls defining a passage extending from a rearward end to a forward end and relative to which said syringe may pass between a rearward, retracted position in which a forward tip of the needle is located within an interior of the passage rearward of said forward end so as to be shrouded by said passage and a forward, extended position in which said forward tip projects from the forward end of said passage; a plurality of elongate transverse projections within the interior of said passage and projecting inwardly from an inner surface of the wall of the passage at an intermediate position between said forward end and said rearward end of the passage to reduce a cross-section of the passage; and a removable cap initially disposed at the front end of the device and having a plurality of elongate fingers which when the cap is in its initial position extend rearwardly down the passage to engage the boot, wherein said fingers are angularly interspersed with said transverse projections.

17. The injection device according to claim 16, wherein the walls of the passage comprise a needle shroud element which is relatively movable to the body portion.

18. An injection device comprising: a body portion;
a syringe having a forward end and a needle at the forward end; and
a needle shroud element which is movable relative to the body portion and forwardly biased by a forward bias element,
wherein the needle shroud element includes a wall that defines a passage extending from a rearward end to a forward end and relative to which said syringe is passable between
i) a rearward retracted position in which a forward tip of the needle is located within an interior of the passage rearward of said forward end so as to be shrouded by said passage and
ii) a forward extended position in which said forward tip projects from the forward end of said passage,
wherein when the syringe is in the forward extended position, the needle shroud element is movable to an extended position in which the forward tip of the needle is located within the interior of the passage rearward of said forward end so as to be shrouded by said passage, wherein said passage, defined by said needle shroud element, includes a plurality of transverse projections within the interior of said passage and projecting inwardly, from an inner surface of the wall at an intermediate position between said forward end and rearward end of the passage, that reduce a cross-section of the passage, with the projections including resiliently deflectable portions inclined inwardly towards the forward end of the passage, and
wherein at least forward ends of all of the resiliently deflectable portions are forward of the forward tip of the needle when the syringe is in the rearward retracted position.

19. The injection device according to claim 18, wherein,
the needle shroud element is telescopically mounted on the body, and
the needle shroud is initially held against the forward bias element in the rearward retracted position whereby the forward end of the needle shroud element is proximal to a forward end of the housing.

* * * * *